United States Patent [19]
Hilpert

[11] Patent Number: 5,321,166
[45] Date of Patent: Jun. 14, 1994

[54] METHOD FOR THE PRODUCTION OF ALDEHYDES

[75] Inventor: Hans Hilpert, Reinach, Switzerland

[73] Assignee: Hoffmann-La Roche Inc., Nutley, N.J.

[21] Appl. No.: 18,999

[22] Filed: Feb. 18, 1993

[30] Foreign Application Priority Data

Mar. 3, 1992 [CH] Switzerland .............................. 664/92

[51] Int. Cl.⁵ ....................... C07C 45/43; C07C 45/42
[52] U.S. Cl. .................................... 568/490; 568/449; 568/484
[58] Field of Search ................ 568/449, 484, 488, 490

[56] References Cited

U.S. PATENT DOCUMENTS

| | | | |
|---|---|---|---|
| 4,211,727 | 7/1980 | Entwistle et al. | 568/490 |
| 4,760,196 | 7/1988 | Fukumoto et al. | 568/484 |
| 4,950,799 | 8/1990 | Hargis | 568/484 |
| 5,059,716 | 10/1991 | Joentgen et al. | 568/490 |

FOREIGN PATENT DOCUMENTS 0246504 11/1987 European Pat. Off. .

*Primary Examiner*—Werren B. Lone
*Attorney, Agent, or Firm*—George M. Gould; William H. Epstein; Bruce A. Pokras

[57] ABSTRACT

A process for the manufacture of aldehydes by the catalytic reduction of carboxylic acid halides with hydrogen in the presence of an alkylene oxide.

9 Claims, No Drawings

METHOD FOR THE PRODUCTION OF ALDEHYDES

The manufacture of aldehydes by the catalytic hydrogenation of carboxylic acid halides, especially chlorides, is known as the Rosenmund reaction. Hydrogen halide (chloride) which results in this reduction poses problems in the use of the reaction. First, the resulting hydrogen halide reduces the yield of the desired aldehyde, insofar as this is acid-labile, or makes the reaction wholly unsuitable for the manufacture of such aldehydes. Second, on safety grounds and taking into consideration the corrosive properties of the hydrogen halide, particular technical measures can be required in the removal of the hydrogen halide from the reaction mixture, e.g., in a hydrogen stream.

The neutralization of the hydrogen halide by the addition of conventional bases results in poor yields of the final aldehyde when carboxylic acid halides which are base-labile are used as the starting material.

It has now been found that the catalytic hydrogenation of carboxylic acid chlorides to aldehydes can be carried out advantageously in the presence of alkylene oxides.

The process in accordance with the invention is especially suitable for the conversion of acid-labile or base-labile carboxylic acid halides to the corresponding aldehydes. Acid-labile and base-labile carboxylic acid halides include compounds having a functional group protected by a protecting group wherein the protecting group can be hydrolyzed by the presence of acid or base. Examples of acid-labile and base-labile protecting groups are the conventional hydroxy-protecting groups and the conventional amino-protecting groups which are removed at the end of a synthesis by hydrolysis. Thus, in accordance with the present invention, carboxylic acid halides which contain functional groups protected by acid or base-labile protecting groups can be reduced to the corresponding aldehyde without loss of the protecting groups.

Examples of acid-labile aldehydes are aldehydes which contain functional groups which are protected by acid-labile protecting groups, such as carbamate groups (e.g., 2-trimethylsilylethyl carbamate, tert.butyl carbamate and 1-methyl-1-(4-biphenylyl)ethyl carbamate groups), or aminoacetal groups (e.g., N-methoxymethylamino, pivaloyloxymethylamino or N-tetrahydropyranylamino groups), or phosphinamido groups (e.g., N-diphenylphosphinylamino).

In addition, the process of the invention is also suitable for the reduction of carboxylic acid halides which contain functional groups, such as an α-amino group, which readily react with the resulting aldehyde group under acidic or basic conditions.

Acid-labile and base-labile aldehydes also include those aldehydes in which the aldehyde-group itself may undergo further reactions, such as the Cannizzaro reaction, aldol condensation, etc. in the presence of acid or base, or which have chiral centers which undergo racemization in the presence of acid or base.

The invention accordingly comprises a process for the manufacture of aldehydes by the catalytic reduction of carboxylic acid chlorides with hydrogen in the presence of an alkylene oxide.

The reduction is preferably carried out in the presence of $C_{2-6}$-alkylene oxides, especially butylene oxide, propylene oxide or ethylene oxide.

The process in accordance with the invention can be carried out under the reaction conditions which are known per se for the Rosenmund reaction. Preferably, the reduction is carried out at room temperature and normal pressure. The process in accordance with the invention is conveniently carried out in the presence of an inert organic solvent. Examples of such solvents are hydrocarbons such as petroleum ether or toluene; or halogenated hydrocarbons such as methylene chloride. As the catalyst there can be used conventional noble metal catalysts, especially palladium, conveniently on carriers such as $BaSO_4$ or charcoal. The use of palladium on charcoal, e.g., 5% Pd on charcoal, is preferred. The aldehyde formed can be separated from the reaction mixture obtained after the hydrogenation in a manner known per se, e.g., by extraction.

The invention is illustrated in more detail by the following Examples.

EXAMPLE 1

1 mol of 1,2-butylene oxide and 23.5 g of Pd/C (5% Pd) were added to a solution of 0.5 mol of 3-phenyl-2(S)-phthalimidopropionyl chloride in 1200 ml of toluene. The suspension was hydrogenated at room temperature and atmospheric pressure while stirring vigorously for 17 hours, whereby 11.3 l of hydrogen were taken up. Thereafter, the suspension was filtered over a filter aid and the residue was washed with toluene. The filtrate and washings were combined and treated while stirring with a solution of 0.5 mol of sodium pyrosulphite in 1 l of water. After stirring at room temperature for 4.5 hours the phases were separated. The aqueous phase was washed with 500 ml of toluene. The toluene phases were washed with 350 ml of water. The combined aqueous phases were treated with 1400 ml of toluene and 420 ml of 3N sulphuric acid and stirred at 60° for 6 hours. Thereafter, the phases were separated and the aqueous phase was extracted with 500 ml of toluene. The toluene phases were washed with water, combined, dried over $MgSO_4$ and evaporated. There were obtained 97.8 g (70%) of (S)-α-benzyl-1,3-dioxo-2-isoindolineacetaldehyde as a white solid, melting point 115°–117°, $[\alpha]_D^{20} -200°$ (1% in ethyl acetate).

EXAMPLE 2

3-Cyclohexyl-2-(tert.-butoxycarbonylamino)propionaldehyde can be obtained from 2-tert.-butoxycarbonylamino-3-cyclohexylpropionyl chloride in analogy to Example 1.

EXAMPLE 3

N-Phthaloyl-leucinal can be obtained from N-phthaloyl-leucyl chloride in analogy to Example 1.

EXAMPLE 4

1-tert.-Butoxycarbonyl-pyrrolidine-2-carbaldehyde can be obtained from 1-tert.-butoxycarbonyl-pyrrolidine-2-carbonyl chloride in analogy to Example 1.

I claim:

1. A process for the manufacture of aldehydes, which process comprises catalytically reducing a carboxylic acid halide with hydrogen in the presence of a $C_{2-6}$ alkylene oxide to produce said aldehyde.

2. The process of claim 1, wherein the alkylene oxide is butylene oxide, propylene oxide or ethylene oxide.

3. The process of claim 2 wherein the aldehyde is an acid-labile or base-labile aldehyde.

4. The process of claim 3 wherein the carboxylic acid halide is 3-phenyl-2(S)-phthalimidopropionyl chloride and the aldehyde is (S)-α-benzyl-1,3-dioxo-2-isoindolineacetaldehyde.

5. The process of claim 3 wherein the carboxylic acid halide is N-phthaloyl-leucyl chloride and the aldehyde is N-phthaloyl-leucinal.

6. The process of claim 3 wherein the carboxylic acid halide is 1-tert.-butoxycarbonyl-pyrrolidine-2-carbonyl chloride and the aldehyde is 1-tert.-Butoxycarbonyl-pyrrolidine-2-carbaldehyde.

7. The process of claim 3 wherein the aldehyde is an α-aminoaldehyde

8. The process of claim 7 wherein the carboxylic acid halide is 2-tert.-butoxycarbonylamino-3-cyclohexylpropionyl chloride and the aldehyde is 3-cyclohexyl-2-(tert.-butoxycarbonylamino)propionaldehyde.

9. A process for the manufacture of acid-labile or base-labile aldehydes, which process comprises catalytically reducing a carboxylic acid chloride with hydrogen in the presence of an alkylene oxide selected from the group consisting of butylene oxide, propylene oxide and ethylene oxide to produce said aldehyde.

* * * * *